United States Patent [19]

Linke et al.

[11] 4,330,677
[45] May 18, 1982

[54] POLYETHER COMPOUNDS, THEIR PRODUCTION AND THEIR MEDICINAL USE

[75] Inventors: Siegfried Linke; Mithat Mardin; Hans P. Krause; Rudiger Sitt, all of Wuppertal, Fed. Rep. of Germany

[73] Assignee: Bayer Aktiengesellschaft, Leverkusen, Fed. Rep. of Germany

[21] Appl. No.: 89,839

[22] Filed: Oct. 31, 1979

[30] Foreign Application Priority Data

Nov. 18, 1978 [DE] Fed. Rep. of Germany ....... 2850058

[51] Int. Cl.³ .............................................. C07C 59/00
[52] U.S. Cl. ..................................... 562/583; 560/45; 560/46; 560/64; 560/170; 560/263; 560/264; 562/426; 562/427; 562/431; 562/465; 562/466; 562/553; 562/556; 562/581; 562/582; 562/586; 564/346; 564/349; 564/457; 564/462; 564/505; 568/45; 568/46; 568/61; 568/62; 424/307; 424/308; 424/309; 424/317

[58] Field of Search ............... 562/581, 583, 564, 426, 562/427, 431, 465, 466, 553, 556, 582, 586; 424/317, 313, 307, 308, 309; 564/346, 349, 457, 462, 505; 560/263, 264, 170

[56] References Cited

U.S. PATENT DOCUMENTS

| 2,010,154 | 8/1935 | Hubacher | 560/186 |
| 2,653,972 | 9/1953 | Ash | 560/186 |
| 3,959,460 | 5/1976 | Vanlergerghe et al. | 562/581 |
| 3,983,171 | 9/1976 | Vanlergerghe et al. | 562/581 |

*Primary Examiner*—Paul J. Killos
*Attorney, Agent, or Firm*—Sprung, Horn, Kramer & Woods

[57] ABSTRACT

The invention relates to polyethers having an an average molecule weight of 3000 to 5000 and having a propylene oxide proportion of 60 to 80% and an ethylene oxide proportion of 20 to 40%. Also included in the invention are compositions containing said polyethers and methods for the use of said polyethers and compositions, particularly for their anti-lipidaemic effect.

16 Claims, No Drawings

POLYETHER COMPOUNDS, THEIR PRODUCTION AND THEIR MEDICINAL USE

The present invention relates to certain new polyether compounds, to processes for their production and their use as lipid absorption inhibitors.

It is already known that surface-active polyethers which consist of propylene oxide units and ethylene oxide units have lipid absorption inhibiting properties. It is pointed out by Bochenek and Rodgers that non-ionic "Pluronic" (Trade Mark) polyols with a hydrophobic block of 90% (that is to say 90% of propylene oxide) have lipid absorption inhibiting actions, whilst the more hydrophillic polyethers from the same series have only a slight influence on lipid absorption (compare Biochimica et Biophysica Acta, 489, (1977) 503–506).

Polyoxyalkylenes which can be used as laxatives are described in U.S. Pat. No. 3,202,578. In addition to the laxative action, an effect of lowering the cholesterol level in blood is also mentioned in this patent specification. According to the statements of this patent specification, those polyoxyalkylenes which have a molecular weight of about 7,500 and contain 80% of ethylene oxide are particularly suitable as compounds which lower the cholesterol level.

According to the present invention there are provided compounds which are polyether derivatives of the general formula

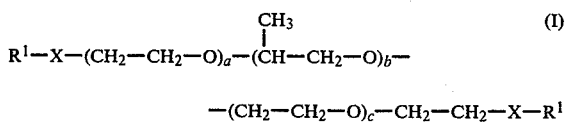

or a salt thereof, in which
X in each case denotes oxygen, sulphur or a NH or N-alkyl group,
$R^1$ denotes an alkyl, alkenyl, cycloalkyl, cycloalkenyl, aryl or aralkyl group, these groups being optionally substituted by nitro, cyano, azido, halogen trifluoromethyl, trifluoromethoxy, phenyl, hydroxyl, amino, alkyl, alkoxy, alkoxycarbonyl, acyloxy, acylamino, hydroxyl, carboxyl or $SO_2$-alkyl, and
a, b and c are integers which are chosen such that an average molecular weight of 3,000 to 5,000 results and that the propylene oxide proportion (b) is 60 to 80% and the ethylene oxide proportion (a) and (c) is 20 to 40%.

More particularly,
X in each case denotes oxygen, sulphur or a NH or N-alkyl group wherein the N-alkyl group contains 1 to 4 carbon atoms,
$R^1$ denotes an alkyl or alkenyl group with up to 12 cabon atoms unsubstituted or substituted by 1 or 2 optionally esterified carboxyl groups; a cycloalkyl or cycloalkenyl group with 5 to 8 ring members; are aryl or aralkyl group in which the aryl portion is mono- or bi-cyclic carbocyclic aryl and the alkyl portion contains 1 to 4 carbon atoms and which is unsubstituted or substituted in the aryl portion being unsubstituted or substituted by $C_1$ to $C_4$ alkyl, alkoxy or alkoxycarbonyl, halogen, nitro, trifluoromethyl, trifluoromethoxy, cyano, azide phenyl hydroxy, amino, $C_1$ to $C_4$-alkanoyloxy oralkenoylamino carboxyl or $SO_2$-alkyl wherein alkyl has 1 to 4 carbon atoms and (a) and (c) are integers between about 9 and 18 and (b) is an integer between about 41 and 55.

In the case where the substituent $R^1$ contains a carboxyl or amino group, the present invention, as indicated, also relates to salts of these compound which are formed either with bases or, in the case of the amino group, with acids. Among the new polyether derivative salts of the invention, these salts that are pharmaceutically acceptable are particularly important and are preferred.

Thus, resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzenesulfonic, toluenesulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Where $R^1$ contains a carboxyl group, salts are, of course, formed in the standard way by reacting the carboxyl-group-containing compounds with especially alkali or alkaline earth metal hydroxides (preferably sodium or potassium hydroxide).

Compounds of the general formula (I) with an average molecular weight of about 4,000, a propylene oxide proportion of 70% and an ethylene oxide proportion of 30% are of particular interest.

Surprisingly, the polyether derivatives of the present invention display a very powerful lipid absorption inhibiting action, in spite of the low molecular weight and an ethylene oxide proportion of 20 to 40%.

According to the present invention there is further provided a process for the production of compounds of the invention in which
(a) a polyether of the general formula

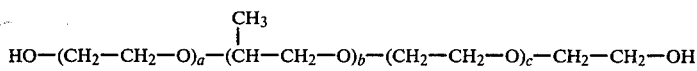

in which
a, b and c have the meaning indicated above, is converted into a corresponding dialcoholate with sodium hydride, sodium amide or a sodium alcoholate in an inert organic solvent and the dialcoholate is then reacted with a halide of the general formula Hal–R$^1$ (III)

in which
R$^1$ has the meaning indicated above and

Hal denotes a halogen atom, preferably a bromine or chlorine atom,
or
(b) the hydroxyl groups of a polyether of the general formula (II) are replaced by halogen atoms according to the following reaction:

II + SOHal$_2$ → IV wherein Hal is Br or Cl, to give a halide of the general formula

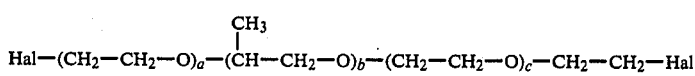

in which
a, b, c and Hal have the meaning indicated above, and this halide is than reacted with an alcohol, mercaptan or amine of the general formula

R$^1$–X–H (V)

in which
R$^1$ and X have the meaning indicated above, in the presence of an inert solvent.

In the case where R$^1$ denotes an aryl group and X denotes oxygen, process variant (b) (reaction of (IV) with (V)) is the preferred embodiment.

If the polyether of the general formula (II), sodium hydride and bromoacetic acid ethyl ester are used as starting materials, the course of the reaction according to variant (a) can be represented by the following equation:

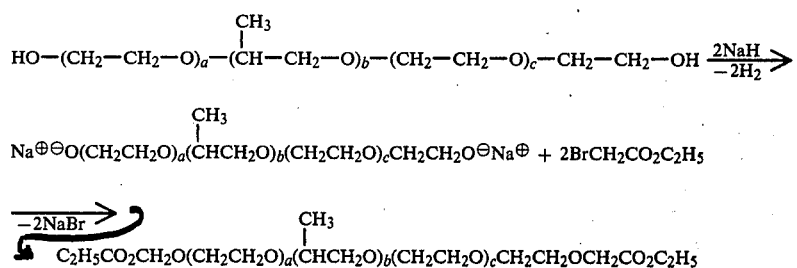

If the polyether of the general formula (II), thionyl bromide and the sodium salt of p-hydroxybenzoic acid ethyl ester are used as starting materials, the course of the reaction according to variant (b) can be represented by the following equation:

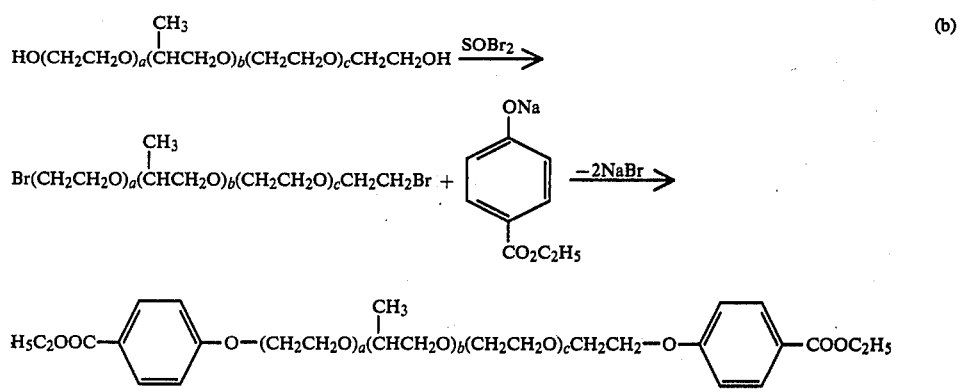
(b)

The polyethers of the general formula (II) to be employed as starting materials are known, or they can be prepared by known methods (compare U.S. Pat. No. 3,674,619 and I. R. Schmolka in J. Am. Oil Chemists Soc. 54, No. 3, 110-16, 1977).

The halides of the general formula (III) to be employed as starting materials are known, or they can be prepared by known methods (compare Houben Weyl 5/3, 830–838, 862–870 (1962); 5/4, 361–411, 610–628 (1960) and The Chemistry of Hydroxyl Group, Part 1, S. 593 (1971).

Examples which may be mentioned are: bromoacetic acid methyl ester, bromoacetic acid ethyl ester, 2- bromo-butyric acid ethyl ester, 4-bromobutyric acid methyl ester, 4-bromocrotonic acid ethyl ester, 2-bromoisobutyric acid ethyl ester, 2-bromopropionic acid ethyl ester, 3-bromopropionic acid methyl ester, 2-bromovaleric acid ethyl ester and 5-bromovaleric acid ethyl ester.

Polyether derivatives of the general formula (I) in which

X denotes oxygen, sulphur, or a NH or N-($C_1$ or $C_2$ alkyl) group and $R^1$ denotes an alkyl group with 1 to 10, in particular 1 to 8, carbon atoms, a benzyl or a phenyl radical, the alkyl radicals optionally being substituted by one or two optionally esterified carboxyl groups and the phenyl radical optionally being substituted by $C_1$ to $C_4$ alkyl (preferably $C_1$ or $C_2$ alkyl), $C_1$ to $C_4$ alkoxy (preferably $C_1$ or $C_2$ alkoxy), halogen, nitro or trifluoromethyl, are of particular importance.

Compounds of the general formula (I) in which

X denotes oxygen and $R^1$ denotes an alkyl group with 1 to 4 carbon atoms which is substituted by a carboxylic acid group, are especially preferred.

The compounds according to the invention have a narrow molecular weight distribution.

Characterisation and establishing the composition of the compounds according to the invention are effected analytically by determining the molecular weight from the hydroxyl number. The ethylene oxide content is determined from the $^1$H—NMR spectrum.

Surprisingly, the polyethers according to the invention exhibit very powerful actions in the treatment of disorders in fat and carbohydrate metabolism. In particular, they cause a lowering of the increased cholesterol level in serum and in tissue and at the same time reduce hypertriglyceridaemia.

The compounds according to the invention are suitable for the treatment of hyperlipoproteinaemia, arteriosclerosis and adiposity and for the treatment of metabolic disorders produced by these diseases.

It must be described as decidedly surprising that the polyethers, according to the present invention have such a pronounced hyperlipidaemic action precisely in this molecular weight range of 3,000 to 5,000, in particular 4,000, and with the particular propylene oxide/ethylene oxide ratio. Since the compounds according to the invention, in addition to having this powerful action, are very well tolerated, they are an advance in pharmacy.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention. "Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a forteith) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules, and pills include the following: (a) fillers and extenders, e.g. starch, sugars, mannitol and silicic acid: (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) absorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glucols and fats (e.g. cocoa oil and high esters (e.g. $C_{14}$-alcohol with $C_{16}$-fatty acid )) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters or sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 20 as sole diluent.

The discrete coherent portions constituting the medicament according to the invention will generally be adapted by virtue of their shape or packaging for medical administration and may be, for example, any of the following: tablets (including lozenges and granulates) pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 25 to 5,000 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example, intramuscularly, intraperitoneally, subcutaneously and intravenously), rectally or locally, preferably orally. Preferred pharmaceutical compositions and medicaments are therefore those adapted for administration such as oral administration. Administration in the method of the invention is preferably oral administration.

In general it has proved advantageous to administer amounts of from 0.05 mg to 500 mg/kg, preferably 0.5 mg to 100 mg/kg, of body weight per day divided into 1 to 6 administrations, preferably immediately before and/or during and/or immediately after meals, to achieve effective results. An individual administration preferably contains the active compound of compounds in amount of 0.1 mg to 100 mg/kg of body weight. Nevertheless, it can at times be necessary to deviate from those dosage rates, and in particular to do so as function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate for the production of compounds of the present invention.

EXAMPLE 1

(Process variant a)

20g of a polyether with the average molecular weight of 4,000 (compound II) are reacted with 3 g of sodium hydride in 100 ml of tetrahydrofurane under nitrogen. After 1 hour, 2.6 g of bromoacetic acid ethyl ester are added and the mixture is then boiled under reflux for 14 hours. After decomposition of the excess sodium hydride, the reaction mixture is evaporated and the residue is chromatographed over the neutral aluminium oxide using chloroform as the running agent. The eluate is evaporated. In the IR spectrum, the residue shows no OH band but a CO band at 1710 cm$^{-1}$. After saponification of the ester groups with sodium hydroxide solution in ethanol, the polyether derivative according to the invention, with two free carboxyl groups is obtained.

$n_D^{20} = 1.4572$; CO at 1710 cm$^{-1}$.

EXAMPLE 2

20 g of the polyether employed in Example 1 are reacted with 3 g of sodium hydride analogously to Example 1 and 2.2 g of methyl iodide are then added. The reaction mixture is purified by chromotography on neutral aluminium oxide. The IR spectrum of the resulting dimethyl ether of the polyether employed no longer contains an OH band.

$n_D^{20} = 1.4561$.

EXAMPLE 3

If bromopropionic acid ester is employed instead of bromoacetic acid ethyl ester and the procedure is analogous to Example 1, after saponification of the two ester groups the propionic acid derivative of the polyether is obtained in an oily consistency and with two free carboxyl groups.

$n_D^{20} = 1.4570$.

EXAMPLE 4

If 2-bromovaleric acid ethyl ester is used instead of bromoacetic acid ethyl ester and the procedure is analogous to Example 1, after saponification of the ester groups the corresponding polyether derivative is obtained in an oily form.

$n_D^{20} = 2.4570$.

EXAMPLE 5

If the alkylating agent ethyl iodide is used instead of methyl iodide and the procedure is analogous to Example 2, the corresponding diethyl ether derivative of the polyether employed is obtained in an oily form and no longer show an OH band.
$n_D^{20} = 1.4563$.

EXAMPLE 6

Using octyl iodide and a procedure analogous to Example 2, the corresponding octyl ether is obtained in an oily form.
$n_D^{20} = 1.4565$.

EXAMPLE 7

Using benzyl bromide and a procedure analogous to Example 2, the corresponding benzyl ether is obtained in an oily form.
$n_D^{20} = 1.4569$.

EXAMPLE 8

(variant b)

80 g of the polyether according to claim 1 are reacted with 5 ml of thionyl bromide. After seperation by chromatography over aluminium oxide, 40 g of a polyether dibromide are obtained, to which, in 100 ml of ethanol, 3 g of sodium hydroxide and 2.4 ml of thioacetic acid ethyl ester are added. After a reaction of 4 hours at 80° C., the corresponding thioether of the acetic acid ethyl ester is formed. Sulphor content: calculated 1.6% found: 1.7%
$n_D^{19} = 1.4702$.

EXAMPLES 9 to 16

If the reaction is carried out analogously to Example 8 and the following thioalcohols are employed instead of thioacetic acid methyl ester, the corresponding thioethers of the polyether (average MW 4,000) are obtained under working conditions analogous to those in Example 8.

| Example 9 | |
|---|---|
| Thiophenol: oil | $n_D^{20} = 1.4763$ |
| Example 10 | |
| 4-Chlorothiophenol: oil | $n_D^{20} = 1.4765$ |
| Example 11 | |
| 4-tert.-Butylthiophenol: oil | $n_D^{20} = 1.4764$ |
| Example 12 | |
| 4-Nitrophenol: oil | $n_D^{20} = 1.4765$ |
| Example 13 | |
| 4-Methylthiophenol: oil | $n_D^{20} = 1.4767$ |
| Example 14 | |
| Mercaptoethanol: oi; | $n_D^{20} = 1.4666$ |
| Example 15 | |
| 3-Trifluoromethylthiophenol: oil | $n_D^{20} = 1.4763$ |
| Example 16 | |
| 4-Methoxythiophenol: oil | $n_D^{20} = 1.4764$ |

EXAMPLE 17

1 l of ethanol saturated with ammonia is added to 36 g of a halide formula (IV) (in which Hal denotes bromine atoms) and the mixture is left to stand at room temperature for 7 days. The alcohol is then stripped off and the reaction mixture is chromatographed on neutral aluminium oxide using petroleum ether/benzene (1:1).
IR: —NH$_2$ st 3200–3300.
$n_D^{20}$; 1.4605.
Nitrogen content: Calculated: 0.7%; Found: 1.0%.

EXAMPLES 18 to 22

If the following amine compounds are employed in Example 17 instead of ammonia, the corresponding amine derivatives of the polyether are obtained by the procedure of Example 17.

| Example 18 | |
|---|---|
| Dimethylamine: oil | $n_D^{20} = 1.4630$ |
| Example 19 | |
| Methylethylamine: oil | $n_D^{20} = 1.4622$ |
| Example 20 | |
| N-Methylaniline: oil | $n_D^{20} = 1.4635$ |
| Example 21 | |
| Octylamine: oil | $n_D^{20} = 1.4630$ |
| Example 22 | |
| N-Ethylcyclohexylamine: oil | $n_D^{20} = 1.4628$ |

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the animal's body to the active compound.

What is claimed is:

1. A polyether derivative of the formula

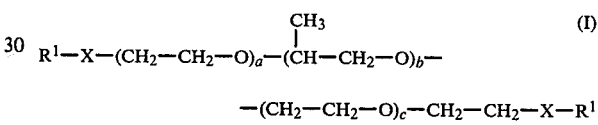

or a salt therof, in which
X in each case denotes oxygen, sulphur or a NH or N-alkyl group containing 1 to 4 carbon atoms;
R$^1$ denotes an alkyl or alkenyl with up to 12 carbon atoms, cycloalkyl or cycloalkenyl, with 5 to 8 ring members, mono- or bi-cyclic carbocyclic aryl, or aralkyl group in which the aryl portion is mono or bi-cyclic carbocyclic aryl and the alkyl portion contains 1 to 4 carbon atoms, these groups being optionally substituted by nitro, cyano, azido, halogen trifluoromethyl, trifluoromethoxy, phenyl, hydroxyl, amino, alkyl with up to 12 carbon atoms, alkoxy with up to 12 carbon atoms, alkoxycarbonyl with up to 12 carbon atoms, acyloxy, acylamino, hydroxyl, carboxyl, or SO$_2$-alkyl and a, b, and c are integers which are chosen such that an average molecular weight of 4,000 results and that the propylene oxide proportion (b) is 70% and the ethylene oxide proportion (a) and (c) is 30%.

2. A compound according to claim 1 in which X denotes oxygen.

3. A compound according to claim 1 in which X denotes sulphur.

4. A compound according to claim 1 in which X denotes NH or N-alkyl.

5. A compound according to claim 1, in which
X denotes oxygen, sulphur or a NH or N-(C$_1$ or C$_2$ alkyl) group and
R$^1$ denotes an alkyl group with 1 to 10 carbon atoms, a benzyl or a phenyl radical, the alkyl radicals optionally being substituted by 1 or 2 optionally esterified carboxyl groups and the phenyl radical optionally being substituted by C$_1$ to C$_4$ alkyl, C$_1$ to C$_4$ alkoxy, halogen, nitro or trifluoromethyl.

6. Compounds according to claim 2, in which $R^1$ denotes an alkyl group with 1 to 8 carbon atoms, a benzyl or a phenyl radical, the alkyl radicals optionally being substituted by 1 or 2 optionally esterified carboxyl groups and the phenyl radical being substituted by $C_1$ or $C_2$ alkyl or $C_1$ or $C_2$ alkoxy.

7. Compounds according to claim 1 in which X denotes oxygen and $R^1$ denotes an alkyl group with 1 to 4 carbon atoms which is substituted by a carboxyl acid group.

8. A pharmaceutical composition containing as an active ingredient an antilipidaemically effective amount of a compound according to claim 1 in admixture with a solid, liquid or liquefied gaseous diluent.

9. A pharmaceutical composition according to claim 1 in the form of a sterile or physiologically isotonic aqueous solution.

10. A composition according to claim 8 or 9 containing from 0.5 to 95% by weight of the said active ingredient 11. A medicament in dosage unit form comprising an antilipidaemically effective amount of a compound according to claim 1 together with an inert pharmaceutical carrier.

12. A medicament of claim 3 in the form of tablets, pills, dragées, capsules, ampoules, or suppositories.

13. A method of combating fat metabolism diseases in warm-blooded animals which comprises administering to the said animals an antilipidaemically effective amount of an active compound according to claim 1 either alone or in admixture with a diluent or in the form of a medicament.

14. A method according to claim 13 in which the active compound is administered in an amount of 0.5 to 100 mg per kg body weight per day.

15. A method according to claim 13 or 14, in which the active compound is administered orally.

16. A compound of claim 1 wherein X denotes oxygen and $R^1$ denotes —$CH_2COOH$.

* * * * *

UNITED STATES PATENT AND TRADEMARK OFFICE
CERTIFICATE OF CORRECTION

PATENT NO. : 4,330,677
DATED : May 18, 1982
INVENTOR(S) : Siegfried Linke et al

It is certified that error appears in the above—identified patent and that said Letters Patent is hereby corrected as shown below:

Column 4, before line 29, Insert --Saponification $$HOOCCH_2-O-(CH_2CH_2O)_a(\overset{\overset{\displaystyle CH_3}{|}}{C}HCH_2O)_b(CH_2CH_2O)_c-CH_2-CH_2-O-CH_2COOH--.$$

Signed and Sealed this

Twenty-first Day of September 1982

[SEAL]

Attest:

GERALD J. MOSSINGHOFF

Attesting Officer

Commissioner of Patents and Trademarks